(12) United States Patent
Schmidt

(10) Patent No.: US 8,001,990 B2
(45) Date of Patent: Aug. 23, 2011

(54) DEVICE FOR MEASURING THERMAL PROPERTIES IN A MEDIUM AND METHOD FOR DETERMINING THE MOISTURE CONTENT IN THE MEDIUM

(75) Inventor: Walter Schmidt, Russikon (CH)

(73) Assignee: Plantcare AG, Russikon (CH)

( * ) Notice: Subject to any disclaimer, the term of this patent is extended or adjusted under 35 U.S.C. 154(b) by 1014 days.

(21) Appl. No.: 11/815,156

(22) PCT Filed: Nov. 9, 2005

(86) PCT No.: PCT/CH2005/000663
§ 371 (c)(1),
(2), (4) Date: Sep. 12, 2007

(87) PCT Pub. No.: WO2006/081693
PCT Pub. Date: Aug. 10, 2006

(65) Prior Publication Data
US 2008/0202220 A1 Aug. 28, 2008

(30) Foreign Application Priority Data

Feb. 2, 2005 (CH) .................................. 0149/05
Jun. 7, 2005 (CH) .................................. 0960/05

(51) Int. Cl.
*G01N 25/64* (2006.01)
(52) U.S. Cl. .................... 137/78.3; 73/75; 374/45
(58) Field of Classification Search ............ 73/73, 75; 137/78.3; 374/45
See application file for complete search history.

(56) References Cited

U.S. PATENT DOCUMENTS 4,013,924 A * 3/1977 Christensen et al. .......... 361/49
5,287,734 A   2/1994 Cuming

FOREIGN PATENT DOCUMENTS

| DE | 25 36 777 | 3/1977 |
| DE | 35 10 379 | 9/1986 |
| DE | 43 40 775 | 6/1995 |
| DE | 101 64 018 | 7/2003 |
| EP | 1 308 085 | 5/2003 |
| JP | 03061845 | 3/1991 |
| WO | 90/13812 | 11/1990 |
| WO | 98/52027 | 11/1998 |

OTHER PUBLICATIONS

Tranlsation of WO98/52027 Nov. 19, 1998 by Fraun-Hofer-Gesellschaft Zur Forderung Der Angewan.*

* cited by examiner

*Primary Examiner* — Craig M Schneider
(74) *Attorney, Agent, or Firm* — Rankin, Hill & Clark LLP

(57) ABSTRACT

The invention relates to a method and device for determining the water content of a medium, particularly of soils and the like, in which a probe or sensor (8) located in the medium is heated. A temporary change in temperature is effected by dissipating the thermal energy through the moisture in the area surrounding the probe, this change in temperature being used for determining the moisture content of the medium. An intermediate layer (13) is placed between the probe and the surrounding medium and is absorbent and mechanically deformable for mechanically coupling the probe to the surrounding medium and for decoupling the probe and the surrounding medium thereby enabling a precise measurement of moisture content to ensue while being subjected to the least possible thermal influence by the largely undetermined surrounding medium.

31 Claims, 4 Drawing Sheets

DEVICE FOR MEASURING THERMAL PROPERTIES IN A MEDIUM AND METHOD FOR DETERMINING THE MOISTURE CONTENT IN THE MEDIUM

BACKGROUND OF THE INVENTION

1. Field of the Invention

The invention relates to a device for determining thermal properties of a medium, in particular humidity sensors, and to a method for the measurement of humidity in a medium, in particular of soil.

2. Description of Related Art

Whilst the measurement of the relative air humidity today is possible in a very simple manner by way of conventional as well as electronic sensors, the measurement of the humidity in mixtures however, in particular of ground or plant substrates, is still problematic.

Electronically functioning humidity sensors mostly operate on the basis of dielectric layers absorbing moisture, which have a dielectric constant which is greatly dependent on the water content. These layers are introduced between two electrode layers which form a plate capacitor and which measure the change of capacitance of this capacitor by way of an applied alternating voltage.

This principle is very suitable for measuring air humidity, but may not however be applied for determining the ground humidity. On the one hand, the sensor would have to be sunk into the ground, wherein a direct gas-permeable connection between the ground and the sensor, as well as a good aeration of the sensor must be guaranteed for a reliable evaluation of the humidity. A direct, gas-permeable connection however creates enormous difficulties. Since the ground may not only be damp, but also wet, the gas connection mostly conceived as a porous filter comes into direct contact with the fluid and becomes blocked. The filter also becomes infested with ground bacteria and ions may migrate through the filter into the sensor region, and destroy it. Furthermore, the sensor including the activation and evaluation electronics is expensive and thus not suitable for large-scale application.

Other methods, as a measurement variable, use the change in the electrical resistance with an increasing humidity of a suitable material absorbing water, such as plaster or nylon, which is brought into contact with the surrounding soil, microwaves of a certain frequency which are locally radiated into the ground, or capacitative sensors which determine the dielectricity constant of the surrounding soil by way of an electrical alternating field. Apart from further disadvantages, all these methods entail high costs and also, to some extent, a considerable technical effort.

For this reason, tensiometer systems are mainly used for measurements of ground substrates. A porous clay-like cell saturated with water is connected by way of a plexiglass tube filled with water to a manometer in an airtight manner, for measuring a vacuum. Due to the contact of the cell with the ground, the existing vacuum of the ground water is transmitted via the clay-like cell and the water filling to the manometer, and may be read there. With an increasing humidity of the ground, the suction tension of the ground water increases, and this is displayed by the manometer as a vacuum.

This principle is used today, in particular in the field of ground humidity measurement in nurseries etc., but also with irrigation systems for balcony and terrace plants, with the following disadvantages. The porous measurements bodies need to be in direct connect with the surrounding substrate over the whole surface, and thus may easily become blocked or also calcified for example with calciferous water. For this reason, they need to be controlled and exchanged again and again. The water supply required for this needs to be controlled and regularly topped up. Furthermore, the manufacturing costs of such a sensor are relatively high and lie in the region of 30-50 Euros. A direct electronic evaluation entails a considerable expense, since for this, the sagging of the membrane needs to be converted into an electronic signal.

Apart from sensors which make use of neutron backscatter and absorption as a measurement principle, there exist yet a series of further sensor principles. The principle of measurement of the thermal conductivity of the ground is also to be found amongst these. This method however has not asserted itself up to now, despite various developments. Thus WO9013812 describes a method with which the soil is located in the inside of a cylinder which is provided with a heating element and a temperature sensor. The heating element produces a heat pulse whose heating effect on the soil is measured with the temperature sensor, and is evaluated as a measure of the humidity. In particular, the thermal conduction is determined to a great extent by the nature and size of the contact surface between the soil and the sensor, which may not be clearly definable. The nature and porosity of the soil also plays an important role.

A further method with the measurement of thermal conductivity is described in JP03061845A2. Thereby, a heating element and a temperature probe are arranged at a certain distance along a measurement rod. The heating element heats the surrounding soil and transports a part of the thermal energy via the surrounding soil to the temperature probe, which indicates a temperature increase. One may deduce the water content of the surroundings by way of this. This sensor too is unreliable since the border surface between the heating element and the soil, as well as between the temperature probe and the soil, is not defined.

In order to avoid the disadvantage of the contact surface between the soil and the sensor, which may not be clearly defined, a method has been developed in DE2536777 with which the temperature probe is surrounded with an artificial standard soil, so that the border surface from the probe to the surroundings is better defined. Thereby, the temperature increase is measured before and after a short heating pulse, and the difference is used for determining the moisture content of the soil. It is also known for the standard soil to be replaced by porous ceramics.

This method has the disadvantage that the difference between the start and end temperature depends on the water content only to a limited extent, i.e. the sensitivity of such a method is very poor. Furthermore, the standard soil itself has a high thermal capacity and thermal conductivity, which influences the measurement.

An inexpensive silicon chip is described in the document WO 98/52027, which is also used as a humidity sensor. In this, the surface of a silicon membrane is covered with an absorbent material in order to lead moisture to the sensor from the surroundings. The measurement surfaces are very small, so that a transition resistance sensor-soil, with a heterogenic soil mixture, is completely random. Furthermore, on measuring, the thermal conductivity of the soil through the thin material dominates, so that the measurement becomes unreliable on account of an undefined (thermal) composition of the surrounding soil.

The document DE 43 40 775 likewise recognizes the fact that a good contact between the sensor housing and the soil is important. Thereby, it is suggested to press the housing walls onto the soil by way of pressure. Thereby however, the substrate is locally compacted and its thermal properties change. Furthermore, soil is often compressible and evades pressure.

If the substrate subsequently dries, the sensor may detach from the substrate, which causes a greatly changed thermal resistance on the border surface.

Other measurement methods such as described in U.S. Pat. No. 5,287,734 for example, use porous ceramics which are arranged between a heating element and a temperature probe. If the ceramics become soaked with the water of the surrounding soil, the thermal conductivity value of the ceramics changes, which gives a conclusion with regard to the water content of the soil. The disadvantage of this method lies in the fact that the ceramics are not enriched with water to an equal extent as the surrounding soil, since the distribution of water-suctioning pores between the soil and the ceramic is very different. Furthermore, pockets of air are formed, since the air may no longer escape from the ceramic body. The sensitivity is poor since only a fraction of the volume of the ceramics is present in the form of pores. The thermal conductivity of the surrounding ground has a great effect on the measurement, due to the relatively high thermal conductivity of the ceramics.

For the above mentioned reasons, and in particular on account of the high costs, none of the methods which are based on the thermal measurement principle have asserted themselves until now.

BRIEF SUMMARY OF THE INVENTION

It is the object of the invention to provide a device for a thermal measurement method, as well as a method for the measurement of humidity in media, which avoid the technical disadvantages mentioned above, and which in particular may be manufactured in an inexpensive manner, are reliable and sensitive with regard to the water content of the surrounding medium.

The object is achieved by the device and the method as are defined in the patent claims.

The invention is based on the measurement principle with a dynamic temperature measurement. For example, an electrical resistance dependent on the temperature is installed into the tip of a measurement probe and is heated to a higher temperature for a brief period of time. The heating may be affected by way of an additional heating element, or also directly by way of a measurement resistance.

With a given heating output, starting from the surrounding temperature, the measurement tip heats up, wherein the temperature increase is generally dependent on the thermal capacity of the sensor itself, on the thermal conductivity of a material enveloping the sensor, as well as on the thermal capacity and thermal conductivity of the surrounding medium. Thermal capacity and conductivity are again dependent on the composition of the surrounding medium, especially on its water content. With a favorable design of the sensor, the main part of the introduced thermal energy is firstly stored in the sensor tip. If the heating is switched off after a given time, the measurement tip cools, wherein the cooling curve permits information on the composition of the surroundings, in particular with regard to its water content. On the other hand, the heating curve may also permit information with regard to the moisture content of the surrounding material.

If the water content is high, the measurement tip on heating will heat up more slowly and after switching off the heating, cools very rapidly again to the surrounding temperature. If the water content is low, the measurement tip heats up more quickly and cools down more slowly.

In principle, different measurement variables or also combinations of these may be used for the electronic evaluation. In principle, one may use the following measurement variables:

a) Temperature increase $\Delta T\ °K$ with a given heating current and heating time. This principle has been known previously, but is less suitable on account of the low sensitivity. b) The heating-up rate in $°K/sec$ on heating, or the cooling-down rate ($°K/sec$) after switching off the heating: These values are not constant over time and are not very sensitive with respect to humidity fluctuations. c) The required heating output (Ws) in order to achieve a certain temperature increase: In order to achieve a high sensitivity with this principle, the heating output must be set quite high which drives up the energy consumption. d) The time (sec) in order to assume a certain temperature again: Since after switching off the heating, the temperature decays exponentially, by way of a suitable selection of a threshold temperature, one may achieve a high spread in this measurement range, and accordingly a high sensitivity of the measurement. In trials therefore, this method of the measurement of the cooling time has been shown to be particularly advantageous. By way of a suitable selection of the threshold value, one may even succeed in the humidity range, which is relevant for the control of the ground humidity, being spread in a special manner, so that the sensitivity is maximized. Furthermore, the energy requirement is minimized on account of a very short heating pulse. The magnitude of the surrounding temperature plays no part due to the measurement of temperature differences.

For optimizing the sensitivity, the following criteria are advantageous for a measurement tip:

The actual sensor region should be designed as small as possible, since with this, the energy required for heating up is minimized, wherein an intermediate storage of thermal energy in the tip may be achieved by way of a micro-thermal heat management in the sensor tip.

The electrical connection to a heating resistance as well as to a measurement resistance should be designed by way of electrical connection conductors which are as thin as possible, so that as little as possible thermal energy may flow off through cables.

The frontmost end of the measurement tip should be well thermally insulated with respect to the remaining measurement tip, since otherwise a thermal mass which is too large is heated up, and the reading accordingly adulterated, i.e. a minimal thermal conduction to the mounting of the actual measurement probe and to the cables should be present.

The measurement tip is provided with a standardized interface to which the thermal energy is released. The interface is arranged between the sensor and the surroundings, so that an influence of different surrounding solid matter media, e.g. soil types such as clay, sand, peat etc. is eliminated or at least greatly reduced. Such an interface which may be attached on a sensor as an exchangeable sheathing, is preferably manufactured of a mechanically elastically deformable, absorbent material such as felt, porous plastic, open-pored polyurethane foam etc., which has a hydrophilic surface, and is preferably homogeneous with regard to the material and density, with an as low as possible thermal conductivity.

The measurement tip as a rule is exposed to a corrosive environment. It or the complete sensor rod should therefore consist of a material which either itself has a long-term good corrosion protection, but also may be rendered corrosion resistant for example by way of a deposited protective layer.

A sensor rod with an introduced sensor should also have a relatively small diameter, in order to simplify the insertion of the rod into the soil or other substrates. On the other hand it should have an adequately high strength, so that it may not buckle on insertion. Furthermore, it is advantageous to attach a marking on the shank of the measurement rod which permits the insertion depth to be read off.

Aluminium is a very good compromise as a material for the sheathing of the tip. It has a relatively good thermal conductivity with a relatively low thermal capacity, is largely corrosion-proof, in particular has a hydrophilic surface and is very easy to process. The material is also very cheap. Other materials such as e.g. stainless steel, brass, ceramic etc. can of course also be used.

As mentioned initially with the description of the measurement principle, a required heating element as a heating resistance may be designed separate from a measurement resistance, or a measurement resistance is simultaneously applied as a heating resistance. In the first case, the activation and the detection of readings is simpler, and in the second case one requires no additional heating resistance with corresponding supply leads. If separate resistances are used, then a so-called thermistor may be used as a measurement resistance, which ensures a very high measurement accuracy.

It has been shown that the thermal coupling between the sensor and the surrounding medium, in particular with sensors which are introduced into a solid matter medium, has an important significance. Mostly, no reproducible reading may be achieved if a sensor tip is inserted into a substrate in an uncovered manner, since the border surface with regard to the size as well as nature is often not defined. A suitable sheathing of the sensor in the form of a suitable interface is therefore extremely advantageous.

Ceramic with a certain porosity, although basically being suitable, however has decisive disadvantages. On the one hand, the ceramic is hard and therefore may not adapt to an environment which is shaped in an irregular manner, e.g. soil. This leads to air gaps and to a size of the border surface which is not defined. On the other hand, ceramic materials (0.15-0.2 W/m° K) have a thermal conduction which is 5 to 10-times higher with respect to air (0.024 W/m° K). This leads to the fact that surrounding material, in particular soil, is also thermally poorly decoupled from the sensor, even in the dry condition. The sensor "feels" the soil even when it is dry. By way of this the sensitivity of the sensor is negatively influenced. A layer thickness between the sensor and soil would have to be selected correspondingly large, wherein layer thicknesses in the region of 5 to 10 mm are usual. Thicker layers may enclose regions which are not yet filled with water, so that the air may no longer escape form these regions. Such in-homogeneities adulterate the reading. A porous ceramic furthermore may only accommodate approximately 30% water. This results in a maximal ratio of the values of the thermal conductivity of water and ceramic of only 1.6 (water and soil have a ratio of approximately 2, thus even higher). Furthermore, the pore distribution in the ceramics is mostly very different compared to the pore distribution in the soil. The soil has a very different pore size distribution, depending on its nature. Apart from very small pores, e.g. in clayey constituents, there are also very large pores in sandy substrates and peat. Porous ceramics as a rule have only very fine pores, by which means they become soaked with water particularly rapidly and become quickly saturated, even with small portions of water in the substrate. It is therefore practically always saturated with water, even if the soil is already quite dry. Furthermore, ceramics do not any more release water in the amount which would correspond to the effective humidity of the substrate. For this reason, porous ceramics indeed are only suitable as an interface for very dry regions.

Due to the mentioned disadvantages of ceramics, a trial was also made to replace these by standard soil as mentioned in DE 2536 777. This is held on the sensor by a net, which is not very practical. Despite a standard soil, the contact surface between the sensor and soil is not well defined, and this changes on account of the water which is introduced on watering. The soil is washed out and changes its thermal properties. Furthermore, the problems with the low sensitivity of measurement are to be taken into account, since it is always the mixture of soil and water which is measured, and the influence of the soil may not be eliminated.

Surrounding media, such as plant substrates, are very heterogeneous mixtures of fine-pored constituents, such as clay etc., constituents with averagely large and large air pores such as peat, compost and also sand, as well as smaller or also larger stones, clumps of soil, etc. The thermal properties of these mixtures vary very greatly, depending on composition, but also their filled weight, i.e. density. Thus a loosely deposited plant substrate has less than half the thermal conductivity in comparison to a compacted substrate. The thermal conductivity of dry substrates varies between 0.3 and 2 W/m° K. Water has a thermal conductivity of 0.6 W/m° K, i.e. a differentiation between the substrate and water is not unambiguous, and therefore a thermal measurement such as described in DE 4340775 is not very conclusive for this reason. If one mixes dry soil with water of 0-100% water constituent, then the thermal conductivity varies between 0.3 and 0.6 W/m° K or 2 to 0.6 W/m° K. In practice however only approximately 50% water may be bound by the soil. The thermal capacity of soil lies in the region of 1-3 Ws/g° K. The value for water is 4.18 Ws/g° K and is therefore significantly higher. A differentiation by way of the difference of the thermal capacity values is however not possible in practice, since it is the thermal conduction which dominates the events. The heat flow from the sensor into the soil is determined by the existing temperature difference, the heat transfer resistance on the border surface, the thermal conductivity of the soil, as well as the effective surface through which the heat may flow. These properties of the soil should thus be taken into account with the measurement of the humidity in soil, in order to obtain reliable readings. This amongst other things is achieved by way of the use of a suitable interface between the sensor and the surroundings, in the form of an optimized material.

A sheathing or an interface should absorb moisture from the surrounding medium and release it again to this medium, and this procedure should preferably largely correspond to that of the soil, i.e. the uptake of water and release of water should be affected analogously and simultaneously to and with the soil. Furthermore, it should be mechanically elastically deformable, so that it adapts to a non-clearly defined surface of a medium, in particular a heterogeneous substance mixture, and for example compensates imprints of stones, or intermediate spaces, of soil, bulk material generally, etc. By way of this, the sheathing also compensates a certain change in volume of the medium, for example due to a drying out or swelling. For this, the material used for a sheathing is open-pored, with preferably the same pore openings as a surrounding solid matter medium, and preferably may be moistened easily with water (hydrophilic). A low thermal conductivity and thermal capacity of the sheathing is also advantageous, since a medium is thermally insulated from a sensor—in the dry condition—by way of this. In particular, materials of fibers such as for example felt, gauze, non-wovens, knitted fabrics and wovens are particularly suitable on account of their low density. Synthetic materials for sheathings are particularly advantageous since they do not rot, or only in a very limited manner. Materials of natural fibers may change their consistency when they dry out, they shrink and may become hard. Moreover, to some part, they rot quite quickly. Material of artificial fibers in contrast are very shape-stable and rot slowly or not at all. An interface material should most preferably be able to be processed in a simple manner, be easily obtainable and as inexpensive as possible.

A sheathing in one preferred form is exchangeably fastened on a sensor and when required may be exchanged, i.e. with appearances of ageing of the material such as calcification or rotting, but also for adaptation to other surrounding media.

In trials, felt has been ascertained to be an excellent material for the sheathing of the sensor. Thanks to its softness, it optimally adapts to an irregular border surface, it is very absorbent and in the dry condition has a very low thermal conductivity value, i.e. surrounding soil is very well thermally insulated from the sensor. Felt layers have a very low thermal conductivity of 0.03 W/m° K, which lies only a little above the value of 0.024 W/m° K of air, and accordingly represent an excellent thermal insulator. In contrast, in the wet condition, the absorbed water becomes dominant due to the low density of the felt. Furthermore, felts are very inexpensive materials which may also be obtained in thick layers. Felts, and generally materials of fibers, in particular nonwoven-like (fleece-like) materials, have the further advantage that the density may be adapted. The absorption behavior may be adapted to that of soil substrates by way of this. If one considers water (0.6 W/m° K) in relation to felt (0.03 W/m° K), a value ratio of 20 results, i.e. with a felt interface one has 10 times the sensitivity compared to soil, and an even higher one compared to ceramics (approximately 12 times). Such a felt or another corresponding interface material, with regard to the thermal properties, behaves essentially as air in the dry condition, and essentially as water in the wet condition.

Felts of synthetic fibers have been ascertained as being optimal in many series of trials, since these may be very resistant to fungi and accordingly do not rot, or only very slowly. Certain fibers also display the property of rapidly absorbing water from the surroundings, but also releasing it to the surroundings again according to its drying out, without a significant difference in the water content between the felt and the soil becoming apparent. The use of felts of aramide fibers has been shown to be particularly advantageous. They unify all the above mentioned advantages.

The sensor may not only be applied for determining the humidity of plant soils, but also for example for monitoring the humidity of a wall, for the exact evaluation of the degree of hardening of concrete, etc. Further application possibilities lie in the field of monitoring bed-wetters, in the field of foodstuff technology, measuring the degree of ripeness of melons etc. The sensor on account of its handiness, its inexpensive design, as well as very high sensitivity is also advantageous in other fields of application, e.g. in which no inhomogeneous surrounding medium is present, for example with evaluations of dew points and monitoring dew points. As soon as the dew point is reached, the water precipitates on the measurement tip, which manifests itself in a change of the cooling curve. The dew point today is usually measured by way of an optical measurement system with a mirror, or with sensors based on electronic humidity sensors which detect the dew point by way of a dielectric layer absorbing moisture. Both types of sensor are expensive, are prone to contamination or corrosion, and are not economically viable, particularly for simpler applications. The above described sensor according to the invention may be manufactured in a very inexpensive manner and furthermore may be encapsulated such that no corrosion or degradation occurs whatsoever. For dew point measurements, the sensor is advantageously designed in a two-dimensional manner. The heating resistance together with the measurement resistance (PCT-resistor) is thermally contacted and encapsulated on a metal lamina. The sensor is at the temperature of the surroundings between the measurements. If the metal lamina is bedewed with an increase of the air humidity or a reduction of temperature, then this is displayed by a temperature increase, since condensation heat is released. This temperature may already be used as proof of the bedewing, wherein the detection accuracy may be significantly increased by way of a bridge circuit with a measurement resistance protected from bedewing. Furthermore, the sensor may be heated by a few degrees, and the temperature course of the cooling curve may be evaluated analogously to the humidity measurements.

The principle according to the invention may also be applied as a wind sensor and rain sensor. If the sensor is designed in a two-dimensional manner and placed perpendicular to the usual direction of the rain, then the surface may be moistened by rain. This may be detected immediately on the measurement curve. The surrounding temperature at the same time is of no significance, since it is a relative measurement which is carried out. In order to obtain a secure proof of the rain, even with the first drop of rain, the sensor surface preferably has an expanse range of approximately 10 cm$^2$. Several sensors may be accommodated in such a surface, which may be read off together or individually.

The sensor may basically be applied whenever a dynamic temperature measurement with an active heating-up of the sensor appears to be meaningful.

The technical advantages of the invention are as follows,

A hermetic encapsulation of the sensor permits its application under difficult environmental conditions. One may prevent a corrosion of the sensor, and thus the life expectancy may be very greatly extended.

The use of a standardized interface, such as felt for example, between solid matter medium surrounding the sensor, such as soil, is not only a technically very simple and also cheap solution, it also results in an excellent sensor performance on account of the thermal separation of the sensor and the surrounding medium.

In a preferred embodiment, the sensor contains no parts which may degrade, or which need to be controlled in a routine manner and exchanged as the case may be.

The sensor signal (resistance change) is very simple to measure, and to evaluate via a micro-controller.

Since a relative measurement is carried out, the surrounding temperature is of no significance. In a preferred embodiment the defined heating output always increases the sensor temperature practically by the same value, independently of the prevailing temperature of the surroundings.

The sensor may be placed in the substrate at each and every depth, i.e. one may determine and control the humidity directly in the region of the roots of plants.

The heating output is typically 50-500 mW, which needs to be brought about over a typical heating time of 5-30 seconds. With measurements which are usually carried out on an hourly basis, this entails a very small average energy requirement.

In particular, the economical advantages are significant. The manufacturing costs in series quantities lie in the region of 1-2 Euros per piece, which is extremely low in contrast to the sensors which are common today. This also means that with larger ground surfaces which are to be monitored, one may apply significantly more sensors at equal costs.

The sensor which is represented here, may be applied in different ways and manners. For the control for example of the ground humidity without any feedback, the sensor is for example connected to an electronic evaluation unit. With this, one may manufacture an apparatus which permits the humidity of solid matter media, such as soil in flower pots, plant pots etc., to be controlled, so that one may always set the correct ground humidity in a manual manner, e.g. for a plant by way of manual watering.

A display unit may be designed in the most varied ways and manners. It may be connected to the measurement rod as a separate apparatus by way of a cable, or the measurement rod and electronics are designed as one unit. Advantageously, the supply of electricity is accomplished by way of integrated batteries. The electricity consumption is very low if the measurement only takes a few seconds.

Since different plants demand different humidities in the root region, one may select between several groups of plants: e.g. dry plants, normal plants, wet plants by way of an integrated selection switch. This setting electronically shifts the optimal humidity range on the display instrument. An actual display consists preferably of an LCD display which may also contain other symbols. For example, on detecting waterlogging or aridness, an alarm signal e.g. in combination with a beep signal or a red alarm light may be triggered. Furthermore, displays may be integrated via the charging condition of the battery.

For the control of the ground humidity with feedback: Such systems are obtainable on the market, but have disadvantages which primarily relate to the applied sensors which do not function in a reliable manner. Furthermore, they are either dependent on a locally available electricity mains with a corresponding splash-water-proof supply lead, and or on a water connection.

The above-described sensor with connected evaluation electronics permits the avoidance of the disadvantages mentioned above, and may be extended into a control circuit for keeping the ground humidity constant, in a simple and very inexpensive manner. Essentially the following additional components are required for this.

An electronic circuit which triggers an action, for example opens a valve or switches on a pump, on falling short of a humidity which is to be defined, for a time duration to be determined by the electronics.

A water supply system which is either connected to the public water mains via a connection, or which may obtain water from a water reservoir via an independent pump, preferably with a return valve.

A water distribution system in the form of tubing, which supplies water to the ground at certain locations. This distribution tubing may also branch off in several branches. With this, a plurality of plant tubs can be supplied with one system. Furthermore, the sensor rod may also be simultaneously used as a supply conduit.

A system which on the one hand is independent of the public electricity supply and on the other hand—if possible— may also exploit collected rainwater for irrigation, has been shown to be a particularly advantageous arrangement. One example of such a system is described hereinafter. It consists of the sensor described above, with evaluation electronics. This is installed in a housing, which apart from the electronics, also contains a submersed pump. The current supply is ensured by batteries, a solar cell which is connected to a battery via charging electronics, or via the electricity mains.

The system additionally contains a selection switch, via which different types of plants with a different water requirement may be set. The system via the sensor determines the actual humidity in the root region of a plant, and from this, whilst taking into account the water requirement of the plant, computes the water quantity to be delivered, i.e. the switch-on duration of the pump, which leads water into the root region of the plant via the distribution system for the computed time. The humidity is increased by way of this. The sensor, at certain time intervals, e.g. every hour or every few hours, redetermines the humidity, and the evaluation electronics via a control algorithm, controls the humidity to a level which is optimal for the plant.

In the case of the supply water due to rain, the humidity is increased without foreign intervention. The closed-loop control installation would then introduce no additional water over a certain time interval, until the optimal humidity is fallen short of. With a downpour lasting a short while, the rain may not seep through to the root region, but rapidly evaporates from the surface region. The control is not adversely affected by way of this.

Due to the extremely low manufacturing costs of the sensor, it is also conceivable for several sensors to carry out measurements at different locations, and thus achieve even more exact values by way of averaging, or in order thus e.g. to irrigate in a surface-selective manner.

Electronics may also additionally ascertain and display various alarm situations, for example:

"No water present": This information may be obtained from the output consumption of the pump; "battery empty", "frost danger": The temperature of the substrate is determined in any case as an initial temperature of a measurement cycle. If this falls below a critical temperature and the ground is at risk of freezing, the alarm is activated. This alarm also indicates that the system needs to be emptied, in order to prevent damage on account of the formation of ice. Furthermore a "manual-on" switch may be provided which serves for permitting the pump to remain switched on over a certain period of time, in order e.g. to pump dry the water supply vessel. The integration of a light sensor, e.g. a simple photodiode, permits the automatic detection of day and night. This information may be used in order to additionally influence the irrigation during the day or night.

If a water supply container is applied, then one may provide this with additional functions.

Automatic refilling from the water mains by way of a float switch, similar to the flush system of a WC.

Installation of a filter system, which filters the water to be delivered by the pump in an adequate manner, so that no accumulations may take place in the pump system.

Installation of a fertilizer supply container, in which depot fertilizer tablets may be introduced. This separate region may be connected to the main volume via small, as the case may be, adjustable holes. The fertilizer tablets dissolve more slowly in the small water volume, but water enriched with fertilizer may seep into the main container through the holes. A very uniform addition of fertilizer may be achieved by way of this.

A filler union protected by a filter, which serves for manual refilling, or however is connected to a rainwater collection installation.

On the one hand an extremely simple assembly and operation with a simultaneous high reliability and very low set-up costs are achieved by way of the elements described above.

BRIEF DESCRIPTION OF THE DRAWINGS

The characteristics according to the invention are hereinafter described in more detail by way of the following exemplary figures, wherein.

DETAILED DESCRIPTION

Figure 1:
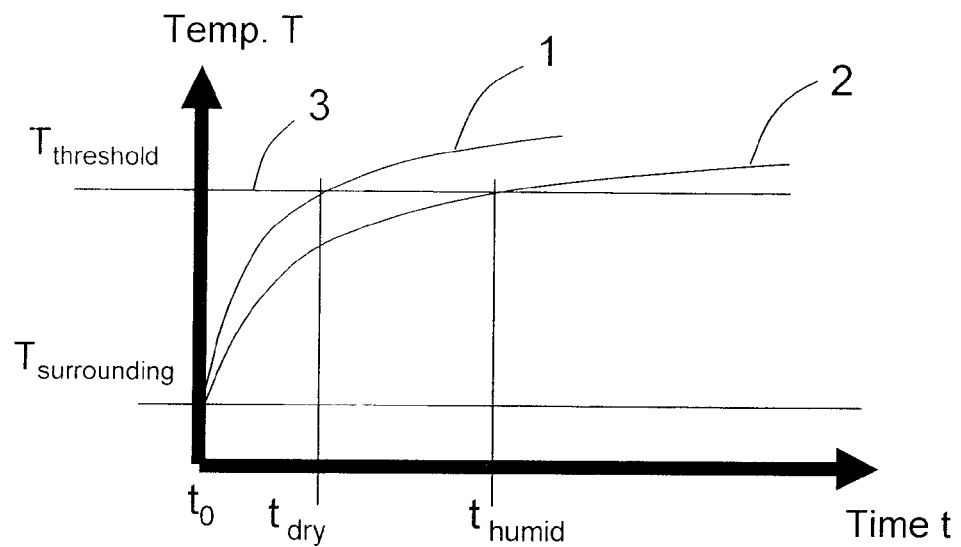
FIG. 1 is a typical course of a curve of temperature, with evaluation of a heat-up phase.

FIG. 1 shows a typical curve course of the temperature on evaluating a heat-up phase with a high and low humidity in a ground sample. A curve 1 shows the temperature course for a substrate with a low moisture content, a further curve 2, the temperature course for a humid substrate. Thus two times, $t_{dry}$ or $t_{humid}$, corresponding to the crossing points of the threshold value with the two curves 1, 2, may be allocated to a temperature threshold value 3, and an action may be triggered on falling below a critical time.

Figure 2:
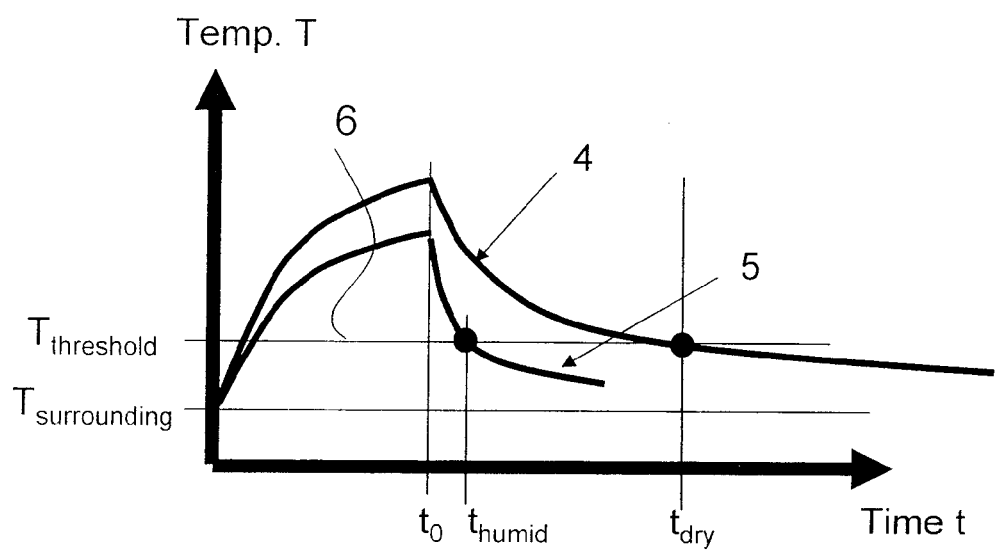
FIG. 2 is a typical course of the curve of the temperature, with the evaluation of a cooling phase.

FIG. 2 shows a typically curve course of the temperature with the evaluation of a cooling phase, with a high and low humidity in a ground sample. A curve 4 in turn shows the temperature curve for a substrate with a low moisture content, and a further curve 5 shows the temperature course for a humid substrate. Again two times, $t_{dry}$ and $t_{humid}$ given by the crossing points of the threshold value with the declining branch of the two curves are allocated to a given temperature threshold value 6, and an action is triggered on falling short of a critical time. The temperature threshold value may either be constant for all degrees of humidity, or however may be selected differently, depending on the degree of humidity.

Figures 3, 4:
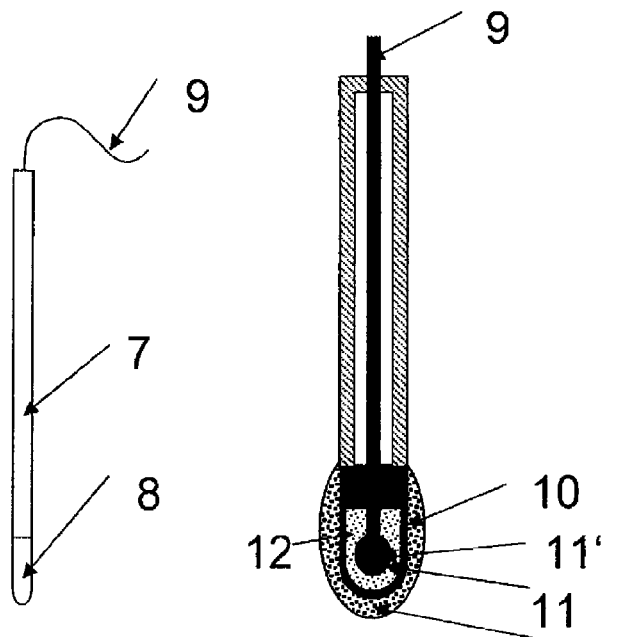
FIG. 3 is a schematically represented sensor rod.
FIG. 4 is a sectioned view through a tip of the sensor rod according to FIG. 3.

FIG. 3 shows a sensor rod 7 with an actual sensor 8 at a tip of the sensor rod 7. The sensor rod 7 at least in the sensor region consists of a thermally poorly conducting material such as plastic, ceramics, etc. One recognizes a cable 9 at the end of the measurement rod 7, which encompasses all wire connections to the heating and to the measurement resistance (not shown in FIG. 3).

FIG. 4 shows a section through the tip or a front part of the sensor rod 7 according to FIG. 3. One recognizes a protective envelope 10 in which a temperature sensor 11 and a heating resistance 11' are bonded in, for example by way of an adhesive 12. The upper, rear end of the sensor rod 7 is only shown schematically. The cable 9 is led out of the hollow sensor rod 7 via a sealing sleeve into an insulated and flexible cable. The tip is provided with an absorbent covering 13, e.g. a felt cap. It is also possible to cover the temperature sensor 8 and measurement resistance 55 which are bonded in as the case may be, with a suitable interface, and to provide this with a reinforced tip or cap. Such a tip preferably comprises only a few thin webs which lead over the interface, and ends in a preferably slightly pointed, more solid tip. Such a tip permits the penetration of the sensor rod 7 into the soil, without the interface or measurement resistance becoming damaged.

Figure 5:
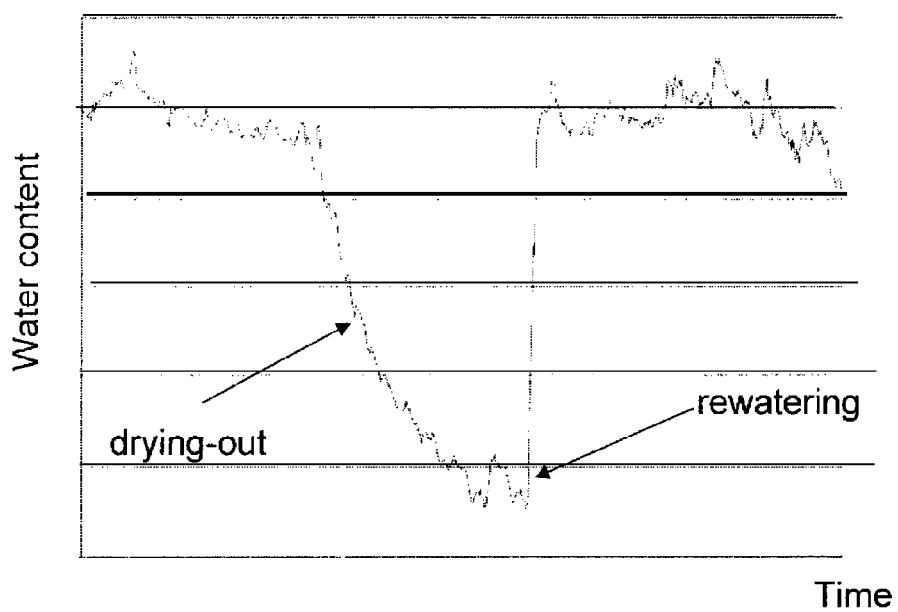
FIG. 5 is a measured course of water content of plant soil.

FIG. 5 shows the course of the water content measured with a device according to the invention, over time, of plant soil in a flower pot, planted with a poinsettia. One may recognize the reduction of the water content, or the drying-out of the soil. After rewatering, the water content increases again in a sudden manner, which is noticeable as a steep rise of the measurement curve.

The time between two measurements is between 0.5-5 hours and the times are typically between 1-2 hours.

Figure 6:
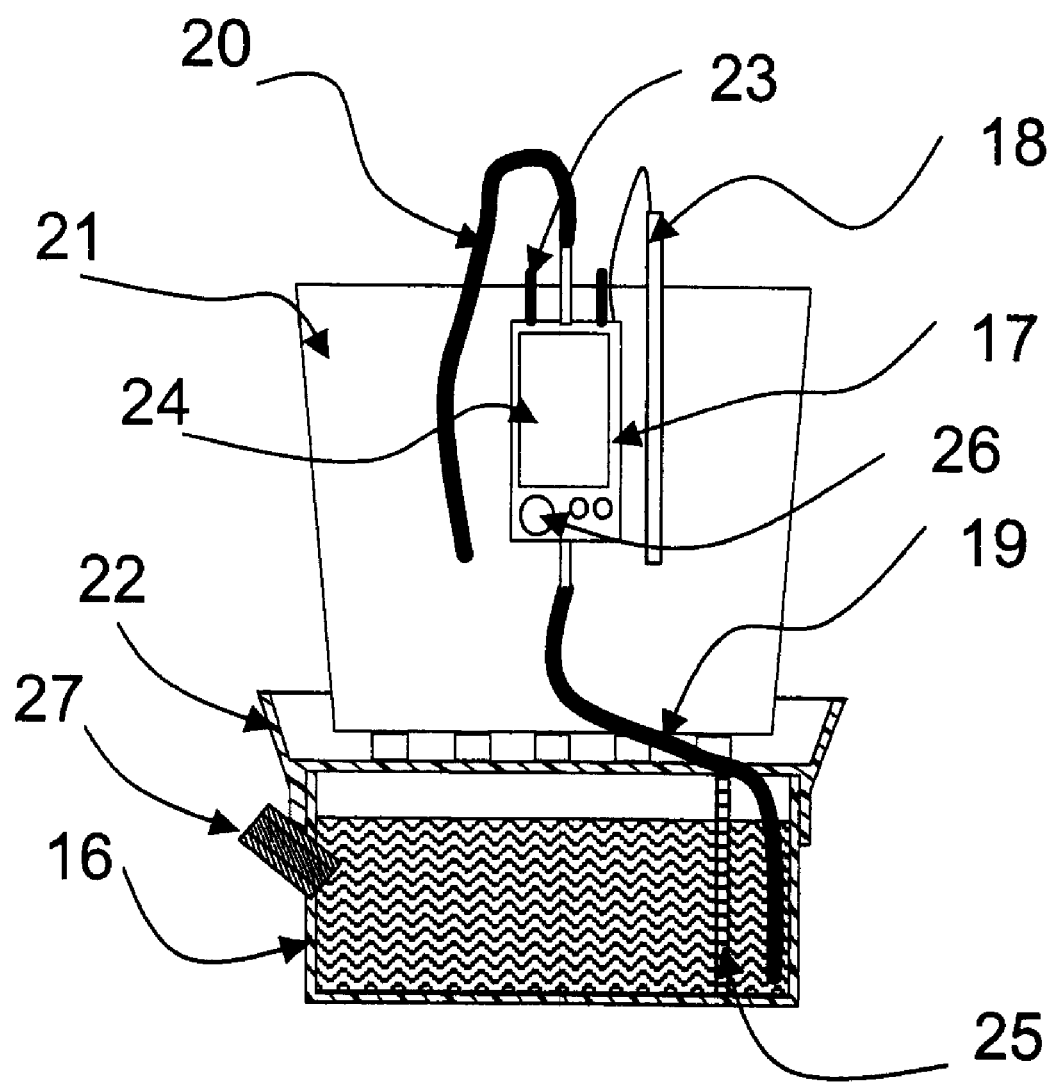
FIG. 6 is a schematic arrangement with essential elements of a control system for automatic irrigation.

In the closed-loop control system shown in FIG. 6 for automatic irrigation, a plant tub 21 stands on a water supply vessel 16. The lid of the vessel 16 is designed as a collection trough 22 for water running out of the plant tub 21. The supply vessel 16 is subdivided by a filter wall 25, wherein water flows into the supply vessel 16 through a filling union 27. The filling union 27 is removed for irrigation on a side of the vessel lying opposite the filter 25. By way of this, one may largely prevent a blockage of conduits, or only small volumes of water may be laced e.g. with fertilizer. A control apparatus 17 is fastened on the plant tub 21 via a simple mechanical fastening 23, e.g. clip bow. The control apparatus 17 contains evaluation electronics for a signal provided by the sensor 18, as well as a pump which via a suction conduit 19 introduces water into the plant tub 21 via a distribution conduit 20. The control apparatus 17 obtains its energy from a solar cell 24 and may contain various operating and display elements 26.

It is of course obvious that the complete control system may also be arranged differently: e.g. the water supply vessel 16 and the plant tub 21 with the collection trough 22 next to one another, and the control apparatus 17 next to or on the plant tub 21. Furthermore the distributor conduit 20 may be divided up into several conduits, so that several plants may be served simultaneously.

Figures 7, 8, 9:
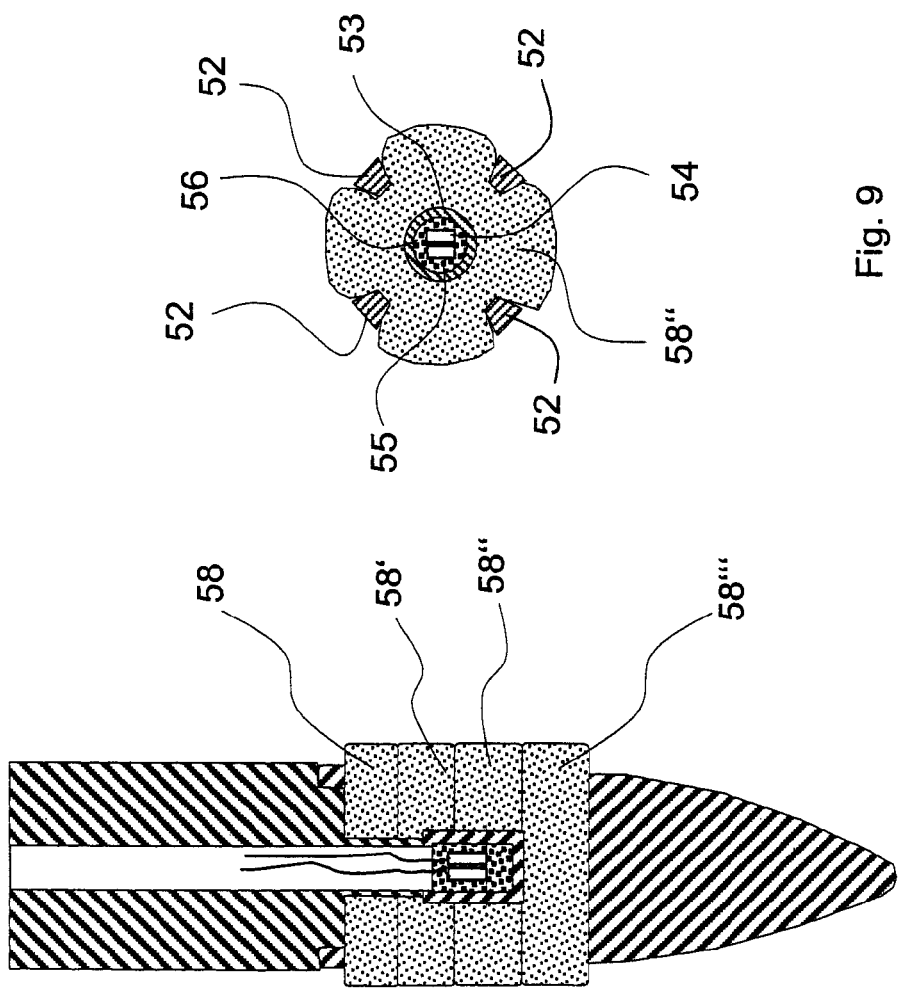
FIG. 7 is a longitudinal section through a front part of the sensor rod.
FIG. 8 is a the longitudinal section according to FIG. 7, with an interface.
FIG. 9 is a cross section through the sensor rod according to FIG. 8.

FIG. 7 shows a longitudinal section through a front region of a further embodiment of the sensor rod 7 according to the invention. A pointed cap 51 is fastened on a shank 50 which has not been completely drawn, preferably with a material or positive fit, in a manner such that where possible, it does not detach from the shank 50, on pulling it out of a compacted soil substrate. The cap 51 permits a simple insertion of the sensor 8 or sensor rod 7 into a substrate. The shank 50 and cap 51 are preferably both manufactured of plastic. The cap 51 in the sensor region has a lantern-like structure, i.e. a cavity 59 formed by the cap 51 comprises several, minimally two, but preferably also three or four cut-outs, so that the cap 51 is only connected to the shank 50 by two or more webs 52. Windows arise by way of this, through which the actual sensor 8 is accessible. The sensor 8 comprises a metallic cover sleeve 53 in which the heating resistance 54 and a measurement resistance 55, preferably positioned back to back, are cast in with a casting mass 56. Wires 57, 57' which are as thin as possible connect the resistances to an activation device.

In order to lead away as little as possible heat energy from the sensor 8 into the shank 50, the shank 50 comprises an extension in the form of a thin-walled tube 60 on which the cover sleeve 53 may be fastened, for example stuck on, and bonded with the cast mass 56. A passage hole 61 present in the shank 50 serves for the supply of the wires 57, 57'. The sensor 8 is optically thermally insulated also on the sides of the shank 50 by way of this.

The heat quantity introduced into the sensor 8 is not immediately released to the surroundings, but to a large extent is intermediately stored in the sensor 8. For this, the fastening of the metal sleeve 53 on the sensor part leading further, is designed as a very thin-walled plastic tube. This largely prevents a discharge of the applied heat energy to the remaining part of the sensor construction. Furthermore, the electrical supply leads to the heating and measurement resistance 54, 55 are designed as very thin copper leads which likewise are only capable of leading a small amount of thermal energy to the rear in the direction of the sensor shank 50. The sensor tip 51 for this reason is also cast out with the cast mass or an adhesive, which permits no direct thermal contact between the heating resistance 54 and the surrounding metal sleeve 53. The heating resistance 54 releases the thermal energy to this cast mass, which subsequently transmits it further to the metal sleeve 53. The heating is switched off at this point in time, and the measurement resistance 54 now measures the temperature reduction due to the further transfer of thermal energy to the felt impregnated with water in the direct surroundings, as shown in FIGS. 8 and 9. Thereby, the soil—in contrast to most other measurement methods—is not heated, as long as the thickness of the felt is only a few mm, i.e. is in a range of 2-6 mm, preferably 3-5 mm, e.g. 4.5 mm. The thickness is selected in a manner such that an influence of the surrounding medium on the measurement may be neglected, thus for example <10%, preferably <5%. The thermal influence of the soil increases with a reducing felt thickness, and the sensor 8 becomes less sensitive and is more greatly influenced by the nature of the surrounding medium.

Exemplary value ranges of densities of felts are 0.05 g/cm$^3$-0.3 g/cm$^3$, advantageously 0.1-0.2 g/cm$^3$, e.g. 0.14 g/cm$^3$. The thickness may be varied accordingly, depending on the density and the nature of the surrounding medium.

FIG. 8 shows a section through the front part of the sensor rod 7, with the sensor 8 after the introduction of an interface. This is an absorbent, mechanically easily deformable material with an as low as possible thermal conductivity, preferably felt. The material in this embodiment is represented in the form of four disks which are layered onto one another, wherein three of these disks 58, 58', 58'' have a central hole in which the sensor 8 is laterally embedded in a peripheral manner. Disk 58''' which lies closest to the frontmost sensor tip 51 has no central hole. The base of the metallic cover sleeve 53 is also covered with felt by way of this. The interface may also be designed differently, e.g. of one piece.

In a cross section through the rod 7 at the height of the sensor 8, it is evident from FIG. 8 and FIG. 9 that the outer diameter of the absorbent felt disks 58, 58', 58'', 58''' is a little larger than the outer diameter of the shank 50 or the sensor rod tip 51, by which means the material is pressed out of the windows between the webs 52. This, on the one hand improves the contact with the surrounding soil substrate, by which means even with looser soil, the moisture is absorbed well, but also the thermal separation to the soil, since the layer thickness of the absorbent material, with a given sensor rod diameter, is further increased around the sensor 8. Furthermore, a pressure of the absorbent material arises in the region of the webs 52 in the direction of the sensor 8, which ensures a good and temporally stable thermal contacting between the felt and the sensor 8. The situation represented in FIG. 9 however also has another significant advantage. Locally more compact zones in the region of the webs 52, and less compact zones in the region of the windows are produced in the partly compressed felt disks, i.e. a whole spectrum of different pore sizes. A significantly better equalization of the pore distribution to that of the soil substrate may be achieved by way of this, and the measurement of the moisture content becomes significantly more accurate.

The shown sensor design reflects the requirements of a thermal measurement procedure also functioning in real soil substrates in an optimal manner. It has an as good as possible thermal insulation of the sensor 8 from the surroundings, including the sensor shank 50 and tip 51. By way of this measure, and an only brief temperature increase of a few degrees, one succeeds in only rendering the direct vicinity of the sensor 8 relevant for the measurement. One may succeed in practically no longer ascertaining any temperature increase at the border surface felt—soil. Furthermore, an optimal extraction of the water from the surroundings is achieved by way of a suitable interface. A border surface which is capable of being mechanically adapted and which forms a reliable moisture bridge even with loose soil or coarse-grained substrate, such as for example expanded clay or porous rock, as is applied for planting, in particular of terraced gardens. The uptake and the release of water at the same rate as with the surrounding substrate is possible by way of the formation of a pore spectrum which is achieved by way of a targeted, local compressing of the absorbent material. A calibration for taking into account the thermal properties of the medium necessary with other measurement methods becomes superfluous, on account on an essentially complete separation of the measurement probe and the surrounding medium, which renders the measurement method simpler and less prone to errors.

It is thus possible with the method according to the invention, not to measure the soil water mixture, but to convey the water from the soil or another, in particular also heterogeneous solid matter medium, into a homogeneous interface, to thermally insulate it and to measure the cooling curve with a great sensitivity.

The invention claimed is:

1. A method for determining the moisture content of a medium, in which a temperature change is produced by heating up a measurement probe, wherein the probe includes a temperature sensor and a heater that are embedded essentially completely and hermetically into an electrically insulating mass which can store heat, the probe being located in the medium, wherein a temporal change in the temperature is effected by way of the leading-away of the thermal energy through moisture in the environment of the measurement probe, and the temporal change is used for determining the moisture content of the medium, wherein between the measurement probe and the surrounding medium an intermediate layer is arranged, which is absorbent and mechanically deformable and which thickness and thermal conductivity is selected in a manner, such that the measurement probe is mechanically coupled to the surrounding medium and thermally decoupled from the surrounding medium, wherein the intermediate layer comprises a felt manufactured of natural or synthetic fibers, and when in use the intermediate layer is in direct contact with the surrounding medium.

2. A method according to claim 1, wherein the intermediate layer is locally deformed in a targeted manner for producing a broad pore spectrum.

3. A method according to claim 1, wherein the temperature change is produced in an insulated, limited volume, and a temporal change in the temperature is effected by way of the leading-away of the thermal energy into the intermediate layer carrying moisture, and the temporal change is used for determining the moisture content.

4. A method according to claim 3, wherein the intermediate layer is locally deformed in a targeted manner for producing a broad pore spectrum.

5. A method according to claim 3, wherein the measurement probe is heated over a defined time duration, and the time duration until reaching an upper temperature threshold is measured, or is left to cool on its own after a defined heat-up phase, and the time duration from switching off the heating until reaching a lower temperature threshold is measured, and wherein the determined time duration until reaching the upper temperature threshold or the lower temperature threshold is a measure of the water content of the medium.

6. A method according to claim 1, wherein the measurement probe is heated over a defined time duration, and the time duration until reaching an upper temperature threshold is measured, or is left to cool on its own after a defined heat-up phase, and the time duration from switching off the heating until reaching a lower temperature threshold is measured, and wherein the determined time duration until reaching the upper temperature threshold or the lower temperature threshold is a measure of the water content of the medium.

7. A method according to claim 6, wherein a longer time duration for reaching an upper temperature threshold indicates a moister medium, and a shorter time duration indicates a dryer medium, and wherein a shorter time duration for reaching a lower temperature threshold indicates a moister medium, and a longer time duration for reaching a lower temperature threshold indicates a dryer medium.

8. A method according to claim 7, wherein an action is triggered on reaching a predefined time duration.

9. A method according to claim 8, wherein the action includes the switching-on of a water supply.

10. A device for determining the moisture content of a medium, comprising at least one measurement probe comprising a temperature sensor and a heater, as well as a circuiting comprising evaluation electronics and a control device, which serves for heating the heatable temperature sensor and for determining the thermal properties of a medium surrounding the measurement probe, wherein the measurement probe is essentially completely surrounded by an absorbent, mechanically deformable and thermally insulating intermediate layer, wherein the intermediate layer comprises a felt manufactured of natural or synthetic fibers, wherein the temperature sensor and the heater are embedded essentially completely and hermetically into an electrically insulating mass, which can store heat, and wherein, when in use, the insulating intermediate layer is in direct contact with the surrounding medium.

11. A device according to claim 10, wherein the intermediate layer is locally compacted in a manner such that a pore size spectrum is present.

12. A device according to claim 10, wherein the intermediate layer is manufactured of aramide fibres.

13. A device according to claim 10, wherein said mass is surrounded by a sleeve of thermally conductive material, and the sleeve is in direct mechanical and thermal contact with the intermediate layer.

14. A device according to claim 10, wherein the thickness of the intermediate layer lies in a range of 3-7 mm.

15. A device according to claim 10, with means for delivering fluids, wherein these means may be actuated by way of actions from the circuiting.

16. A device of claim 10, wherein the device is for determining the thermal conductivity of the surrounding medium.

17. A device according to claim 10, wherein the intermediate layer is homogeneous with regard to its density.

18. A device according to claim 10, wherein the intermediate layer is homogeneous.

19. A device according to claim 18, wherein the intermediate layer is locally compacted in a manner such that a pore size spectrum is present.

20. A device according to claim 10, wherein device parts are designed to be heatable over a certain time in a controlled manner, and to be subsequently coolable automatically, and wherein the circuiting is designed such that apart from the heating, time durations for reaching temperature thresholds may be measured and evaluated.

21. A device according to claim 20, wherein actions may be triggered on reaching a predefined time duration.

22. A device according to claim 10, wherein the intermediate layer is a sheathing that surrounds the measurement probe.

23. A device according to claim 22, wherein the sheathing is exchangeably fastened on the measurement probe.

24. A device according to claim 10, wherein the intermediate layer absorbs and releases moisture, and is open-pored.

25. A device according to claim 24, wherein the material layer is homogeneous.

26. A device according to claim 24, wherein the intermediate layer is manufactured of aramide fibres.

27. A device according to claim 24, wherein said mass is surrounded by a sleeve of thermally conductive material, and the sleeve is in direct mechanical and thermal contact with the intermediate layer.

28. A device according to claim 24, wherein the thickness of the intermediate layer lies in a range of 3-7 mm.

29. A device according to claim 24, wherein device parts are designed to be heatable over a certain time in a controlled manner, and to be subsequently coolable automatically, and wherein the circuiting is designed such that apart from the heating, time durations for reaching temperature thresholds may be measured and evaluated.

30. A device according to claim 24, with means for delivering fluids, wherein these means may be actuated by way of actions from the circuiting.

31. A device according to claim 24, wherein the material layer is homogeneous with regard to its density.

* * * * *